(12) United States Patent
Forsell

(10) Patent No.: US 9,452,081 B2
(45) Date of Patent: Sep. 27, 2016

(54) OSTOMY ACCESSORY

(76) Inventor: Peter Forsell, Zug (CH)

( * ) Notice: Subject to any disclaimer, the term of this patent is extended or adjusted under 35 U.S.C. 154(b) by 301 days.

(21) Appl. No.: 12/682,340

(22) PCT Filed: Oct. 10, 2008

(86) PCT No.: PCT/SE2008/000575
§ 371 (c)(1),
(2), (4) Date: Apr. 9, 2010

(87) PCT Pub. No.: WO2009/048386
PCT Pub. Date: Apr. 16, 2009

(65) Prior Publication Data
US 2010/0217213 A1   Aug. 26, 2010

Related U.S. Application Data

(60) Provisional application No. 60/960,766, filed on Oct. 12, 2007, provisional application No. 60/960,764, filed on Oct. 12, 2007, provisional application No. 60/960,765, filed on Oct. 12, 2007, provisional application No. 60/960,767, filed on Oct. 12, 2007.

(51) Int. Cl.
*A61F 5/445*    (2006.01)
*A61F 5/44*     (2006.01)
*A61F 2/00*     (2006.01)
*A61M 1/00*     (2006.01)

(52) U.S. Cl.
CPC .............. *A61F 5/445* (2013.01); *A61F 2/0036* (2013.01); *A61F 5/4404* (2013.01); *A61M 1/0023* (2013.01); *A61F 2005/4455* (2013.01); *A61M 2202/068* (2013.01); *A61M 2210/106* (2013.01); *A61M 2210/1064* (2013.01)

(58) Field of Classification Search
CPC ................... A61F 5/445; A61F 2005/4455
USPC ................... 604/332, 319, 333–345
See application file for complete search history.

(56) References Cited

U.S. PATENT DOCUMENTS

| | | | | |
|---|---|---|---|---|
| 2,223,566 A | * | 12/1940 | Koch | 604/277 |
| 2,741,247 A | * | 4/1956 | Marsan | 604/344 |
| 3,415,299 A | * | 12/1968 | Hinman, Jr. et al. | 206/324 |
| 3,750,194 A | * | 8/1973 | Summers | 623/23.66 |
| 3,828,782 A | * | 8/1974 | Polin | 604/103.03 |
| 3,938,521 A | * | 2/1976 | Ritota et al. | 604/328 |
| 4,030,500 A | * | 6/1977 | Ronnquist | 604/328 |
| 4,119,100 A | * | 10/1978 | Rickett | 604/103.03 |

(Continued)

FOREIGN PATENT DOCUMENTS

| | | | |
|---|---|---|---|
| DE | 19732982 A1 | * | 2/1999 |
| WO | 97/34646 A1 | | 9/1997 |

(Continued)

OTHER PUBLICATIONS

English translation of DE 19732982A1 to Huelser Feb. 18, 1999.*

(Continued)

*Primary Examiner* — Paula L. Craig

(57) ABSTRACT

The invention discloses an ostomy accessory (13) for an intestinal stoma of a mammal patient, and comprises an insertion portion (8) for inserting into an intestinal stoma (3) of an ostomy, and also comprises an evacuation portion (9, 9' adapted to evacuate fecal matter from an intestine connected to said intestinal stoma through said insertion portion.

15 Claims, 6 Drawing Sheets

(56) References Cited

U.S. PATENT DOCUMENTS

| | | | |
|---|---|---|---|
| 4,314,558 A * | 2/1982 | Korpman | 604/332 |
| 4,344,434 A * | 8/1982 | Robertson | 604/334 |
| 4,555,242 A * | 11/1985 | Saudagar | 604/103.08 |
| 4,634,421 A * | 1/1987 | Hegemann | 604/34 |
| 4,676,802 A * | 6/1987 | Tofield et al. | 604/332 |
| 4,721,508 A | 1/1988 | Burton | |
| 5,261,898 A * | 11/1993 | Polin et al. | 604/328 |
| 5,269,774 A | 12/1993 | Gray | |
| 5,336,203 A * | 8/1994 | Goldhardt et al. | 604/247 |
| 5,466,229 A * | 11/1995 | Elson et al. | 604/317 |
| 5,509,888 A * | 4/1996 | Miller | 600/29 |
| 5,520,669 A * | 5/1996 | Mulholland | 604/328 |
| 5,941,860 A * | 8/1999 | Wheeler | 604/327 |
| 6,050,982 A * | 4/2000 | Wheeler | 604/332 |
| 6,461,292 B1 * | 10/2002 | Forsell | 600/31 |
| 6,464,628 B1 * | 10/2002 | Forsell | 600/30 |
| 6,482,145 B1 * | 11/2002 | Forsell | 600/30 |
| 6,485,476 B1 * | 11/2002 | von Dyck et al. | 604/332 |
| 6,527,755 B1 * | 3/2003 | Salama | 604/348 |
| 6,840,923 B1 * | 1/2005 | Lapcevic | 604/319 |
| 6,896,651 B2 * | 5/2005 | Gross et al. | 600/30 |
| 6,915,165 B2 * | 7/2005 | Forsell | 607/40 |
| 7,235,044 B2 * | 6/2007 | Forsell | 600/29 |
| 7,513,894 B2 * | 4/2009 | Howlett | 604/355 |
| 7,572,218 B2 * | 8/2009 | Schrag | 600/31 |
| 7,722,586 B2 * | 5/2010 | Mullejans et al. | 604/342 |
| 8,075,539 B2 * | 12/2011 | Nishtala et al. | 604/328 |
| 8,696,543 B2 * | 4/2014 | Forsell | 600/37 |
| 8,798,763 B2 * | 8/2014 | Forsell | 607/61 |
| 8,825,173 B2 * | 9/2014 | Forsell | 607/61 |
| 8,862,241 B2 * | 10/2014 | Forsell | 607/60 |
| 2002/0091365 A1 * | 7/2002 | McNally et al. | 604/332 |
| 2003/0009221 A1 * | 1/2003 | Forsell | 623/14.13 |
| 2003/0220621 A1 | 11/2003 | Arkinstall | |
| 2004/0039348 A1 * | 2/2004 | Kim et al. | 604/264 |
| 2004/0078012 A1 * | 4/2004 | Uno | 604/317 |
| 2004/0171999 A1 * | 9/2004 | Andersen et al. | 604/332 |
| 2005/0187578 A1 * | 8/2005 | Rosenberg et al. | 606/232 |
| 2005/0192642 A1 * | 9/2005 | Forsell | 607/40 |
| 2005/0216042 A1 * | 9/2005 | Gertner | 606/151 |
| 2005/0256465 A1 * | 11/2005 | Perlo et al. | 604/327 |
| 2006/0047180 A1 * | 3/2006 | Hegde et al. | 600/30 |
| 2008/0269698 A1 * | 10/2008 | Alexander et al. | 604/332 |
| 2011/0015475 A1 * | 1/2011 | Hanuka et al. | 600/32 |
| 2011/0087337 A1 * | 4/2011 | Forsell | 623/23.68 |

FOREIGN PATENT DOCUMENTS

| | | |
|---|---|---|
| WO | 01/00260 | 1/2001 |
| WO | 01/45487 | 6/2001 |
| WO | 01/58390 | 8/2001 |

OTHER PUBLICATIONS

International Search Report for PCT/SE2008/000575, mailed Mar. 4, 2009.

Notification of Office Action in corresponding Chinese Application No. 200880119933.5, mailed Aug. 25, 2011.

* cited by examiner

OSTOMY ACCESSORY

This application is the U.S. national phase of International Application No. PCT/SE2008/000575, filed 10 Oct. 2008, which designated the U.S. and claims priority to U.S. application Ser. No(s). 60/960,766, filed 12 Oct. 2007, 60/960,764, filed 12 Oct. 2007, 60/960,765, filed 12 Oct. 2007 and 60/960,767, filed 12 Oct. 2007, the entire contents of each of which are hereby incorporated by reference.

TECHNICAL FIELD

The present invention discloses an ostomy accessory.

BACKGROUND

In anatomy, a natural stoma is any opening in the body, such as the mouth, and essentially any hollow body organ can be surgically manipulated into an artificial stoma, if and as necessary. Examples of such organs are the esophagus, stomach, duodenum, ileum, colon, pleural cavity, ureters, and kidney pelves.

One well-known form of an artificial stoma is a colostomy, which is a surgically-created opening in abdominal wall where the large intestine exits, which allows the removal of feces out of the body, bypassing the rectum, to drain into a pouch or other collection device.

A stoma, as explained above, refers to a mouth-like part or opening, and in particular, it relates to a surgical procedure involving the gastrointestinal tract, GIT, or gastrointestinal system, GIS. The GIT begins at the mouth or oral cavity and continues until its termination, which is the anus. Such a surgical procedure is usually undertaken as a result of, and as a solution to, a disease in the GIT. The procedure involves bisecting the GIT or GIS, usually between the later stage of the small intestine, the ileum, and the large intestine or colon, hence colostomy, and exiting it from the body in the abdominal region.

The point of exiting is then a surgically created stoma. For the greatest success, and in order to minimize negative effects, it is preferable to perform this procedure as far down in the tract as possible, as this allows the optimal amount of natural digestion to occur before eliminating faecal matter from the body.

Traditionally, the stoma is usually covered with a removable pouching system (adhesive or mechanical) that collects and contains the output for later disposal. Modern pouching systems enable most individuals to resume reasonable normal activities and lifestyles after surgery. However, traditional pouching systems still cause a patient some discomfort.

SUMMARY

It is an objective of the present invention to alleviate the discomfort caused by traditional pouching systems used by patients who have been through an ostomy procedure. The present invention is primarily intended for use by patients who have been through a novel kind of ostomy procedure, which has also been invented by the inventor of the present invention, but the present invention could also be used by patients who have been through a traditional ostomy, such as for example, a ileostomy.

The novel ostomy procedure mentioned will be explained briefly in one of the following sections of this text, in order to facilitate the understanding of the present invention.

However, the present invention achieves its objective by means of an ostomy accessory for an intestinal stoma of a mammal patient which comprises an insertion portion for inserting into an intestinal stoma of an ostomy, and also comprises an evacuation portion which is adapted to evacuate faecal matter from an intestine connected to said intestinal stoma through the insertion portion.

In one embodiment, the insertion portion is adapted to be inserted into an ostomy reservoir created by said intestine. In one embodiment, the insertion portion is suitably in one embodiment adapted to be inserted into an artificial ostomy reservoir.

Suitably, the insertion portion is adapted to be inserted into an artificial closure made in said intestine proximal to said stoma in order to open and close said intestine.

In one embodiment, the insertion portion is tube-like or tube shaped, and in one embodiment the evacuation portion comprises a substantially collapsible expandable reservoir, such as an expandable bag or a pouch, which in one embodiment is self expandable.

In one embodiment, the evacuation portion comprises an evacuation pump, for evacuation into a reservoir which is external or internal to the accessory of the invention.

BRIEF DESCRIPTION OF THE DRAWINGS

The invention will be described in more detail in the following, with reference to the appended drawings, in which.

DETAILED DESCRIPTION

The accessory of the present invention may be used by patients who have been through traditional ostomy procedures, and have hitherto thus been forced to use a pouch which is attached to a stoma on their abdomen.

However, the invention is also intended for patients who have been through a novel ostomy procedure, which will be explained briefly first, in order to facilitate the understanding of the present invention.

Figure 1:
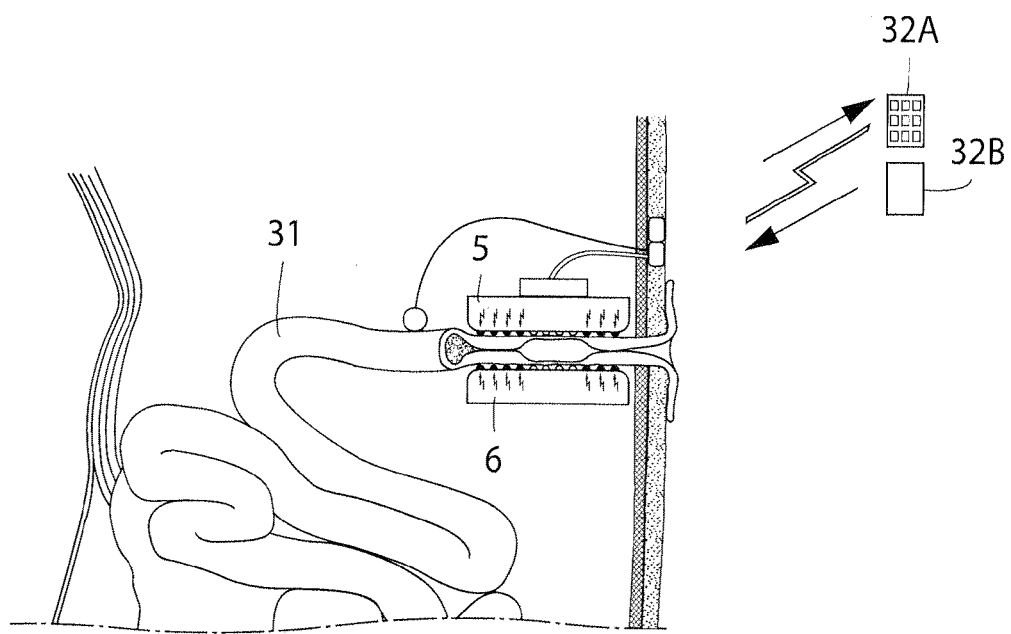
FIG. 1 shows a cross section of a novel ostomy.

FIG. 1 shows a cross section of a part of the abdomen of a patient who has been through the novel ostomy procedure. As can be seen in FIG. 1, the novel procedure, in similarity to traditional ostomy procedures, involves making an opening in an intestine 31 of a patient, as well as creating an opening in the abdomen of the patient, and then arranging a stoma or orifice in the abdominal wall of the patient.

As can be seen in FIG. 1, parts of the intestine are suitably attached to the outside of the abdomen, in order to assist in creating the stoma. This is primarily similar to a traditional ostomy procedure. However, as opposed to traditional ostomy procedures, the novel procedure comprises arranging a constriction device in the abdomen of the patient, with the constriction device being able to open or close access between the intestine and the stoma. As shown schematically in FIG. 1, the constriction device may for example comprise first 5 and second 6 constriction parts, which cooperate to cause the intestine to constrict, thereby closing access between the intestine and the stoma.

When and as needed, the patient may cause the constriction device to open, i.e. to let the first 5 and second 6 constriction parts to distance themselves from each other, so that there is essentially free passage between the intestine and the stoma, and the patient can also cause the constriction device to close. The operation of the constriction device can be carried out by means of a remote control 32A, 32B.

In order to enable a patient who has been through the novel procedure to live without a pouch on the outside of their abdomen, the novel procedure will also suitably comprise arranging a reservoir for faecal matter inside the patient's abdomen.

Figure 2:
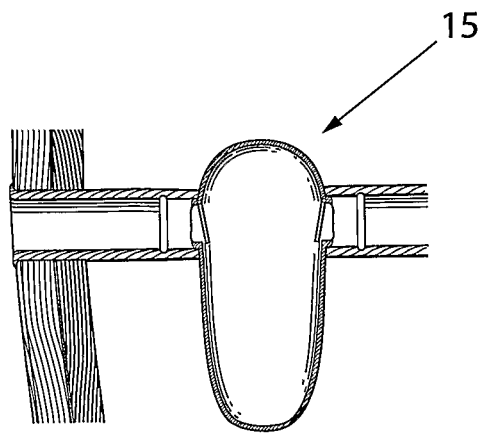
FIGS. 2 and 3 show details of a novel ostomy.
Figure 3:
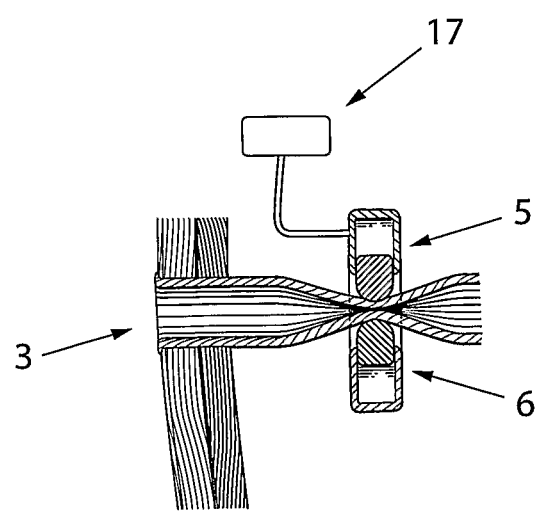

Such a reservoir can be made either from the patient's own intestine, or by implanting an artificial reservoir before the constriction device. Such a reservoir 15 is shown schematically in FIG. 2, with a constriction device 5, 6, being shown schematically in FIG. 3, together with a remote control 17 for the constriction device. In FIG. 3, the stoma or opening 3 is also shown schematically.

Figure 4:
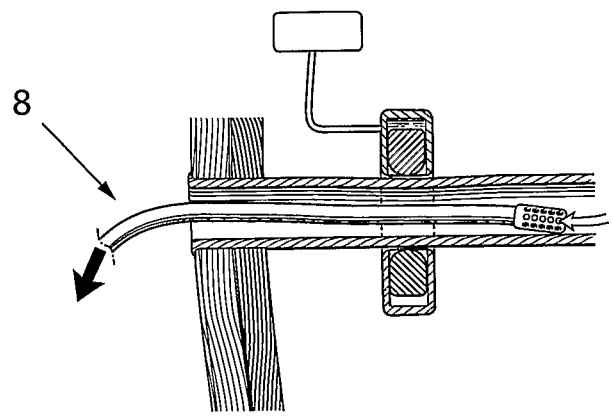
FIGS. 4-8 show details of the invention in use.

In order to evacuate all or parts of the reservoir 15, a patient can use a device such as a remote control 17 in order to open the constriction device 6, to enable outside access to the reservoir 15. p The accessory of the present invention is used to accomplish the evacuation of all or parts of the reservoir 15, in a manner which will now be explained:

The inventive accessory comprises an insertion portion 8 for insertion into the stoma 3 of an ostomy. This is shown in FIG. 4, with the insertion portion 8 being shown as inserted through the stoma 3, and into the artificial closure created by means of the constriction device, which in FIG. 4 has been opened in order to admit access of the insertion portion 8 into or adjacent to the reservoir 15. As also shown in FIG. 4, the insertion portion 8 is suitably tube-like or tube shaped, although other shapes are also within the scope of the present invention.

Figure 5:
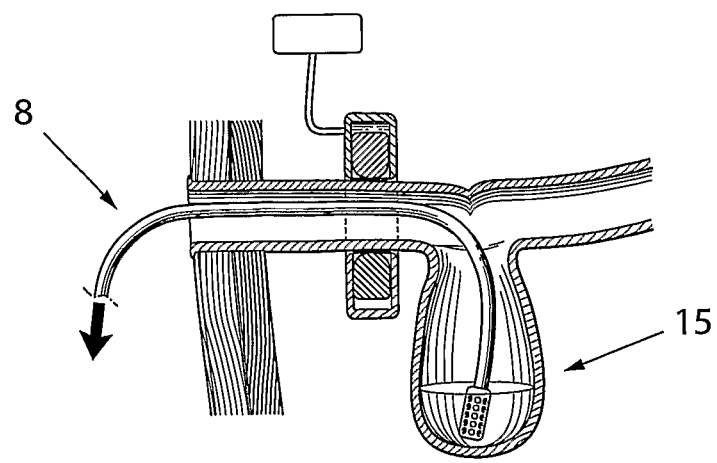

In FIG. 5, one end of the insertion portion 8 is shown as being inserted into the ostomy reservoir 15. As mentioned previously, the reservoir 15 can either be surgically created from an intestine of the mammal, or it can be an artificial reservoir which has been implanted into the mammal.

In order to accomplish the evacuation, the accessory of the invention also comprises an evacuation portion for evacuating all or parts of the reservoir 15 through the insertion portion 8. The evacuation portion can be designed in various ways within the scope of the present invention, but in one embodiment, as shown in FIGS. 6a and 6b, the evacuation means comprise a collapsible vessel 9 such as a substantially collapsible but expandable reservoir, for example an expandable bag or a pouch, which is shown in FIG. 6a in a collapsed state and in FIG. 6b in an expanded state, as being attached to one end of the insertion portion 8.

Suitably, such a collapsible vessel is self expandable and is also a disposable accessory, which may also be the case for the entire accessory of the invention. Also, the insertion portion 8 and the evacuation portion 9 may be one unit, or they may be detachable from each other.

Figure 6A:
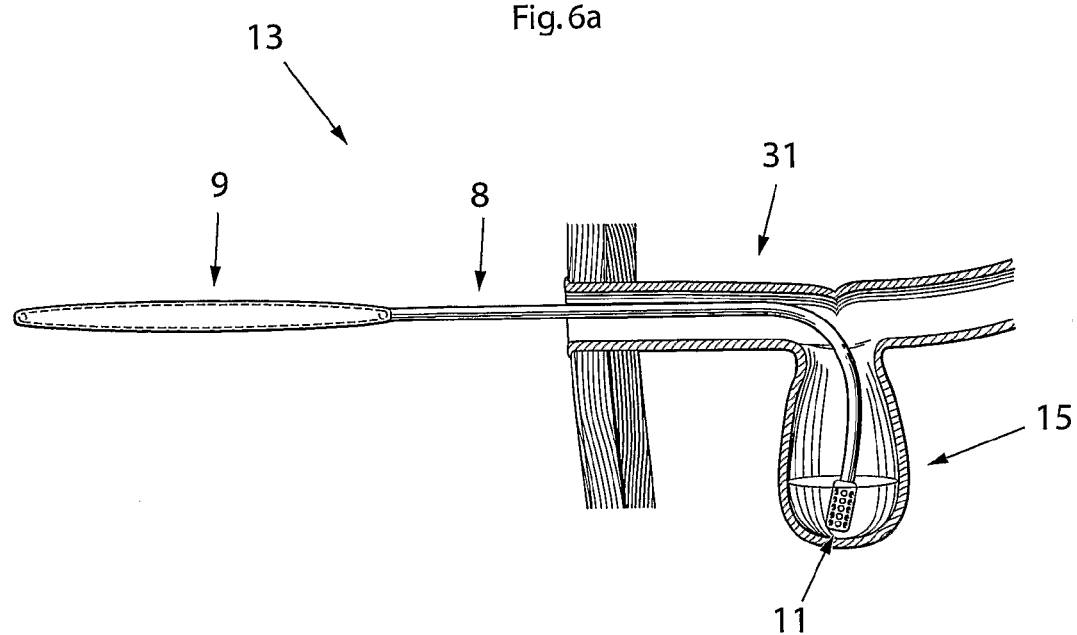
Figure 6B:
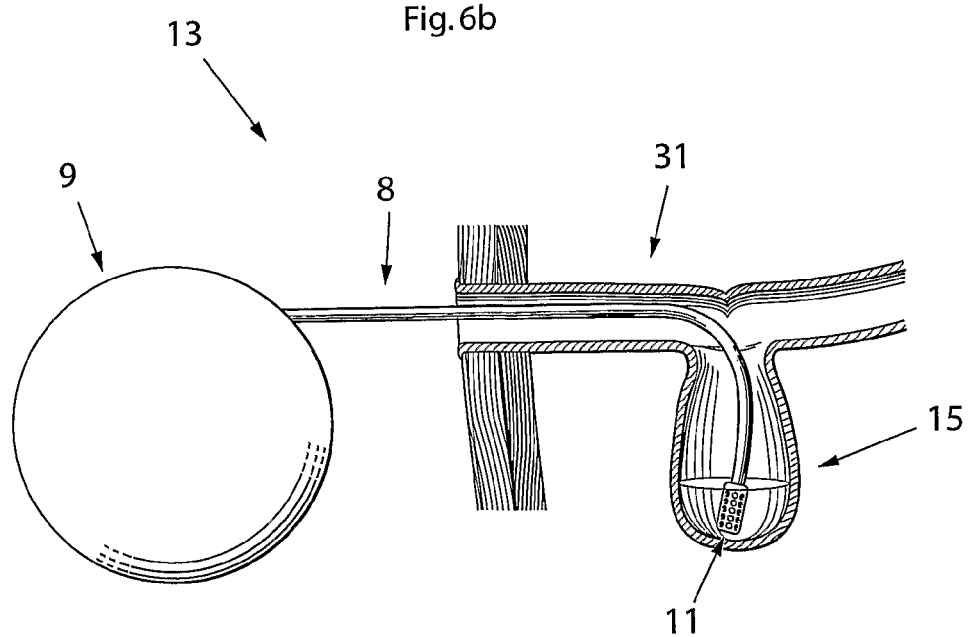

As can be seen in FIGS. 6a and 6b, in, for example, the embodiment with the expandable reservoir 9 which is a part of the accessory, the insertion portion 8 comprises a first opening 11 at the end which is to be inserted into the reservoir 5. If the evacuation portion, i.e. the reservoir 9, is detachable from the insertion portion 8, the insertion portion 8 will also comprise a second opening for attachment to the evacuation portion 9, which in this embodiment will also comprise a first opening.

Figure 7:
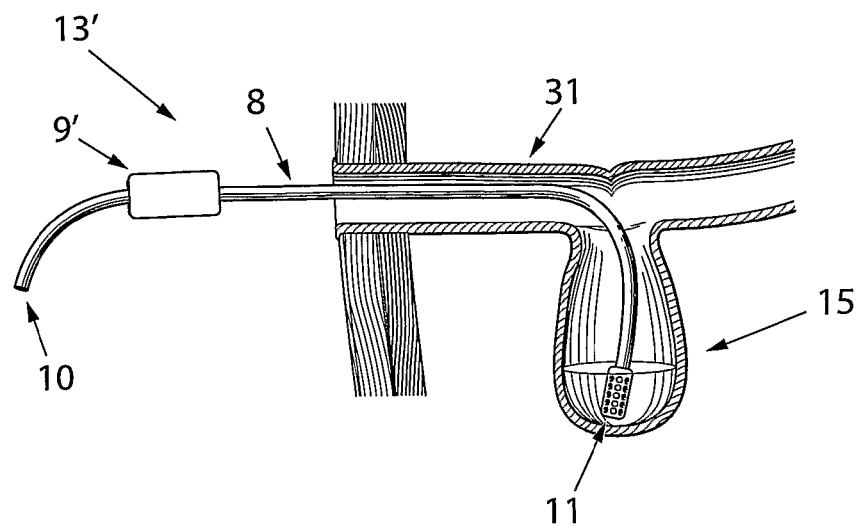

As shown in FIG. 7, in an alternative embodiment of the present invention, the evacuation means may comprise an evacuation pump 9', for evacuation into a reservoir which is external or internal to the accessory of the invention.

Such an evacuation pump 9' may be designed in a variety of ways, and can, for example, be powered by a battery, from a regular power outlet, or by being attached to a water tap which will create a negative pressure on the "reservoir side" of the pump, which will assist in the evacuation.

In FIG. 7, a second 10 opening of the insertion portion 8 is shown, with the second opening 10 being towards the evacuation portion. In fact, in this embodiment, the evacuation portion may also be located inside the tube-like insertion portion, so that the insertion portion is essentially a conduit in which there is arranged a pump. In this case, the second opening of the insertion portion is on the "evacuation side" of the pump 9', such an opening being shown as 10 in FIG. 7.

Naturally, the evacuation portion may also comprise a pump for attachment to the opening 10 of the insertion portion 8, or the evacuation portion may comprise a pump and a tube like portion for attachment to the insertion portion. In the latter case, the evacuation portion should also comprise first and second openings, one or both of which can be made closable.

Thus, in the embodiment with the collapsible vessel, the evacuation is done into the vessel 9, while in the "pump embodiment", the evacuation may be done into a destination of the user's choice, which may of course also be an expandable, collapsible vessel which is attached to the accessory of the invention.

The first 11 and second 10, openings of the insertion portions may suitably be designed so that at least one of them is closable. In the "pump embodiment", both of the openings can then be kept closed until the accessory is to be used, while the same would true for the first opening 11 in the embodiment with the collapsible vessel. The closing of one or more end can be done by means of built-in closing means, or by means of, for example, lids or caps.

Naturally, in the embodiment with the collapsible vessel, if the collapsible vessel is detachable from the insertion portion, then both the first and the second end can be made closable.

Figure 8:
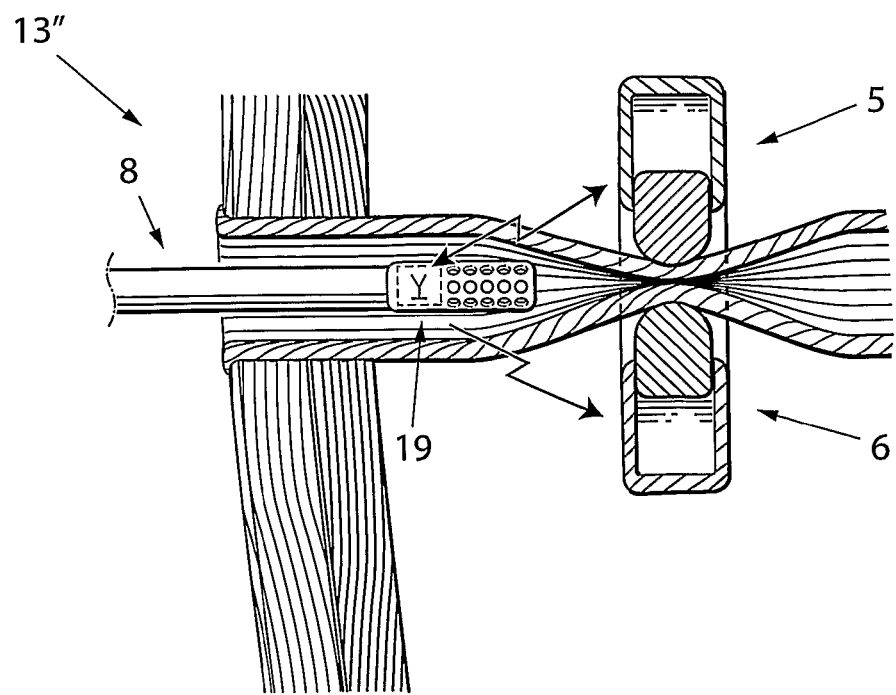

FIG. 8 shows a further embodiment 13" of the present invention. As has been explained above, the accessory of the invention is adapted for use together with a reservoir 15, with outside access to this reservoir being closed or opened by means of a constriction device 5, 6. Thus, in order for the constriction device to allow access by the accessory of the invention, the constriction device must be opened, which as explained above, may be done by means of a control device, such as the remote control 32A, 32B of FIG. 1 or 17 of FIGS. 2 and 3.

However, in the embodiment 13" of FIG. 8, the accessory of the invention comprises a transmitter 19 for accomplishing the opening of the artificial closure, i.e. for opening the constriction device.

In one embodiment, the transmitter 19 is a transmitter of an electromagnetic signal such as a radio signal, while, in one embodiment the transmitter 19 is a transmitter of an ultrasound signal. The choice of transmitter is naturally dependent on the design of the constriction device.

In one embodiment, the transmitter 19 is an active transmitter, i.e. a powered transmitter, but the transmitter may also be a passive transmitter, i.e. a transmitter which reflects a signal emitted by the constriction device in order to "recognize" the transmitter 19.

In a further embodiment, the accessory of the invention accomplishes the opening of the constriction device by means of a mechanical part, i.e. a "key" which interacts with a corresponding mechanical part of the constriction devoice in order to accomplish said opening.

Figure 9:
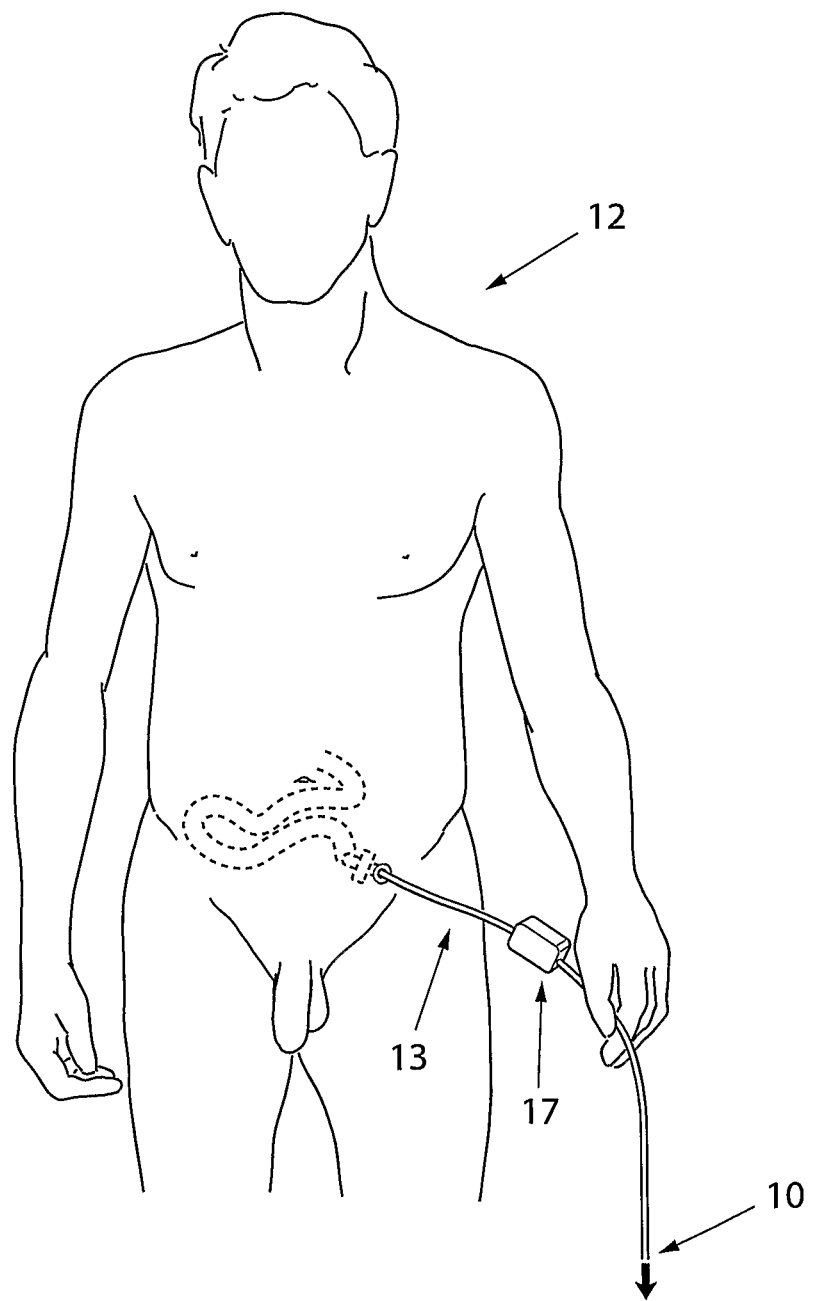
FIG. 9 shows the invention in use by a patient.

FIG. 9 schematically shows a user 12 with an accessory 13 of the invention in the "pump embodiment", with the insertion portion 8 having been inserted through the stoma into the reservoir 5. The pump is symbolically shown in FIG. 8. As shown by means of an arrow, evacuation may now take place through the second opening 10.

The invention is not limited to the examples of embodiments described above and shown in the drawings, but may be freely varied within the scope of the appended claims.

The invention claimed is:

1. An ostomy accessory for an intestinal stoma of a mammal patient, the accessory comprising:
   an insertion portion adapted to be inserted into an natural intestinal stoma of an ostomy,
   an evacuation portion adapted to evacuate fecal matter from said insertion portion and from an intestine connected to the intestinal stoma of the patient, the intestine being formed to an ostomy reservoir, wherein the insertion portion being adapted to be inserted into the ostomy reservoir created by the intestine, the insertion portion further being adapted to cause the intestine to open for flow of the fecal matter out of the intestinal stoma when the insertion portion is positioned into the stoma, and
   a wireless transmitter adapted to communicate with a wireless receiver, the wireless transmitter adapted to co-operate with and open an artificial closure acting on the outside of the intestine, when the insertion portion is positioned adjacent to or in indirect, contact therewith, to allow the fecal matter to be evacuated through the intestine and stoma rising the ostomy accessory, upon a wireless signal sent from the wireless transmitter.

2. The accessory of claim 1 wherein said insertion portion is further adapted to be inserted into an artificial ostomy reservoir.

3. The accessory of claim 1 in which said evacuation portion comprises one opening.

4. The accessory of claim 3, in which said evacuation portion further comprises at least a second opening, with at least one of said first and second openings being adapted to he closed and opened.

5. The accessory of claim 1, in which said evacuation portion comprises at least one of a substantially collapsible expandable reservoir, an expandable bag and a pouch.

6. The accessory of claim 5, in which said collapsible expandable reservoir is self expandable.

7. The accessory of claim 1, in which said evacuation portion comprises an evacuation pump, for evacuation into a artificial second reservoir which is external or internal to the accessory.

8. The accessory of claim 1, in which said transmitter is a transmitter of at least one of an electromagnetic signal, a radio signal and an ultrasound signal.

9. The accessory of claim 8, in which said receiver is an active and powered receive.

10. The accessory of claim 9, wherein the active receive reflects a signal emitted by the evacuating ostomy accessory such that the evacuating ostomy accessory recognizes the receiver.

11. The accessory of claim 8, in which said receiver is a passive receiver.

12. The accessory of claim 1, in which said transmitter is an active and powered transmitter.

13. The accessory of claim 1, in which said transmitter is a passive transmitter.

14. The accessory of claim 13, wherein the passive transmitter reflects a signal emitted by the artificial closure in order to recognize the transmitter.

15. The accessory of claim 1, wherein the wireless transmitter is placed in the insertion portion of the ostomy accessory.

* * * * *